United States Patent [19]

Fine et al.

[11] 4,374,822

[45] Feb. 22, 1983

[54] ORAL COMPOSITION

[75] Inventors: Ralph Fine, East Brunswick, N.J.; Sidney Weiss, Levittown, Pa.

[73] Assignee: Colgate-Palmolive, New York, N.Y.

[21] Appl. No.: 327,668

[22] Filed: Dec. 7, 1981

Related U.S. Application Data

[63] Continuation-in-part of Ser. No. 312,211, Oct. 19, 1981, abandoned.

[51] Int. Cl.$^3$ ............................ A61K 7/16; A61K 7/26
[52] U.S. Cl. .......................................... 424/49; 424/58
[58] Field of Search .............................. 426/634, 650; 424/48–58

[56] References Cited

U.S. PATENT DOCUMENTS

| | | | |
|---|---|---|---|
| 3,340,069 | 9/1967 | Matsuda et al. | 426/650 |
| 3,410,695 | 11/1968 | Shiga et al. | 426/534 |
| 3,421,905 | 1/1969 | Yueh | 426/534 |
| 3,532,515 | 10/1970 | Broderick et al. | 426/533 |
| 3,591,391 | 7/1971 | Kinoshita et al. | 426/650 |
| 3,778,513 | 12/1973 | Shiga et al. | 426/650 |
| 4,022,879 | 5/1977 | Dietrich | 424/49 |
| 4,066,793 | 1/1978 | Eguchi | 426/650 |
| 4,216,200 | 8/1980 | Horn | 424/52 |
| 4,242,323 | 12/1980 | Vlock | 424/58 |
| 4,258,072 | 3/1981 | Eguchi et al. | 426/650 |
| 4,267,195 | 5/1981 | Boudreau et al. | 426/534 |

FOREIGN PATENT DOCUMENTS

| | | | |
|---|---|---|---|
| 45-12267 | 5/1970 | Japan | 426/534 |
| 47-22271 | 6/1972 | Japan | 426/534 |
| 55-131361 | 10/1980 | Japan | 426/534 |
| 4921 | of 1877 | United Kingdom | 424/15 |
| 17875 | of 1909 | United Kingdom | 424/15 |
| 321965 | 11/1929 | United Kingdom | 424/15 |

OTHER PUBLICATIONS

New Gaines Dog Biscuits-Best News for Dogs Since Cats-General Foods Adv., Sunday Star Magazine, Washington, DC., Dec. 4, 1955.

*Primary Examiner*—Shep K. Rose
*Attorney, Agent, or Firm*—Robert L. Stone; Murray M. Grill; Herbert S. Sylvester

[57] ABSTRACT

Oral composition having a mellow flavor characteristic due to the presence of a flavoring oil and a 5'-ribonucleotide as a flavor modifying agent. Early high or flash foaming is also promoted. Typical agents are disodium 5'-guanylate and disodium 5'-inosinate.

12 Claims, No Drawings

ORAL COMPOSITION

This application is a continuation-in-part of application Ser. No. 312,211, filed Oct. 19, 1981, now abandoned.

Oral compositions have been used for many years in the promotion of oral hygiene. To the consumer it is important that the dentifrice be perceived as having a desirable pleasing flavor, since it dwells in the oral cavity in contact with the taste buds during use.

Such flavors have commonly had strong notes, such as the notes of peppermint, spearmint or clove oils, as many people look to such types of tastes. However, these flavors can include some harsh notes, and some users would like to experience or perceive a milder or mellower flavor.

Not every flavor modifying agent can be used in an oral composition. Acceptable materials are developed by both means of art and means of science. The flavor modifying agent must blend well with the varied components of dentifrice flavors and also should be compatible with the several components of the dentifrice, such as surface active agent without undesirable decomposition during storage.

It is an advantage of this invention that a mellow or mild flavor is provided to oral compositions.

It is a further advantage of this invention that an oral composition is provided which can give high initial foam upon introduction into the oral cavity.

Other advantages will be apparent from consideration of the following specification.

In accordance with certain of its objects this invention relates to a flavored oral composition comprising a dental vehicle, a flavoring oil in amount to provide flavor characteristic to said dentifrice up to about 5% by weight of said dentifrice, and about 0.002–0.007% by weight of a 5'-ribonucleotide.

The flavored oral composition may be a dental cream (including gel) in which case the dental vehicle is typically a blend of an aqueous phase of water and/or humectant with a gelling or binding agent, generally with a dentally acceptable water-insoluble polishing agent; a dental tablet, in which case the dental vehicle is typically a binding agent and a dentally acceptable water-insoluble polishing agent; chewing gums, in which case the dental vehicle is typically an art-recognized gum base; tooth powders, in which case the dental vehicle is typically a water-insoluble dental polishing agent, and mouthwashes in which case the dental vehicle is an aqueous-alcohol, typically also including humectant. Other types of oral compositions include candies, lozenges, etc. The dental vehicle material is suitable for introducing the product into the oral cavity. Dental creams and mouthwashes are preferred aspects of the present invention.

The flavoring oil employed in the oral composition may be natural or synthetic, as well as mixtures thereof. Examples of suitable flavoring constituents include the flavoring oils, e.g. oil of spearmint, peppermint, wintergreen, sassafras, clove, sage, eucalyptus, marjoram, cinnamon, lemon, and orange, as well as methylsalicylate. Suitably, flavoring oil may comprise up to about 0.01 to 5% by weight of oral compositions of the instant invention, preferably about 0.1–1.5%.

The flavor note provided by the flavoring oil is modified and made mellower or milder by reducing harshness through the presence of about 0.002–0.007% by weight (about 20–70 ppm) of a 5'-ribonucleotide, preferably about 0.003–0.005%. With amounts less than about 20 ppm, the desired effect may be difficult to detect; with greater amounts than about 70 ppm, the ribonucleotide salt flavor may become increasingly detectable. It is difficult to detect at the preferred range 30–50 ppm.

These flavor-modifying agents are a class of compounds characterized as being phosphate salts of nitrogen glucosides of heterocyclic bases, particularly including nucleic acids (polynucleotides). Typical preferred 5'-ribonucleotides are:

5'-inosinate salt

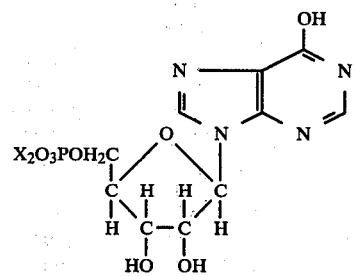

and 5'-guanylate salt

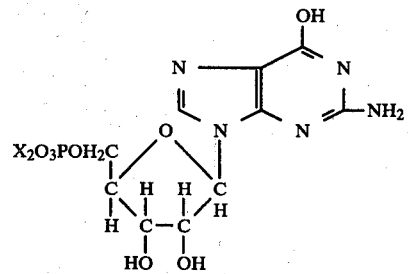

as well as mixtures thereof; wherein X is an alkali metal, ammonium or other oral composition compatible cation such as quaternary ammonium, alkanol ammonium, etc. The preferred cation is an alkali metal, particularly sodium. Disodium inosinate is known in the flavor art as "IMP" and disodium guanylate as "GMP". Other 5'-ribonucleotides include disodium 5'-xanthylate and Disodium 5'-adenylate.

The 5'-ribonucleotides such as IMP and GMP are known to potentiate the flavor of glutamates, such as monosodium glutamate ("MSG") which are widely used in cooking. Such use is described "Biochemical Studies of Glutamate Taste Receptors: The Synergistic Taste Effect of 1-Glutamate and 5'-Ribonucleotides," Cagan et al, *Glutamic Acid: Advances in Biochemistry and Physiology*, Raven Press, New York, 1979, pages 1–7; "The Flavor Enhancer Ribontide R", available from Takeda U.S.A. Inc., 400 Park Avenue, New York, New York, U.S.A.; and "An Introduction to Nucleotide Seasonings: IMP, I & G, GMP" available from Ajinomoto Co., Inc., Tokyo, Japan. The 5'-ribonucleotides potentiate the flavor of glutamates.

Quite unexpectedly it was found that 20–70 ppm of the 5'-ribonucleotide in oral composition functions independently of the presence of glutamates such as MSG, but in conjunction with dentifrice flavoring oils which are chemically quite dissimilar to glutamates and independent of the synergistic cooperative mechanism between glutamates and 5'-ribonucleotides described in the article by Cagan et al, mentioned above. Indeed, the amounts of 5′-ribonucleotides employed in the present invention are substantially less than are generally suggested in its use as a flavor additive.

Moreover, upon introduction into the oral cavity with mild agitating such as toothbrushing or gargling, a high level of initial or flash foam is provided in comparison with a dentifrice which does not contain a 5′-ribonucleotide.

The perceived flavor effect resulting from combination of 5′-ribonucleotide salt and glutamate is synergistic with regard to the positive perceived effect of each separately. 5′-ribonucleotides have not been observed to cooperate synergistically with other materials and the perceived effect found in dentifrices containing flavoring oil, is unexpected, particularly since glutamates are not present.

In addition to flavoring oil and flavor modifying agent, the sialagogue properties of the oral composition may be further modified by the presence of a sweetening agent, in amount such that the sialagogue composed of flavoring oil and sweetener is up to about 5% by weight of the dentifrice. Suitable sweetening agents include sucrose, lactose, maltose, glycerine, sorbitol, perillaritine, xylitol, sodium cyclamate and sodium saccharine.

When the oral composition is a dental cream, chewable tablet or tooth powder, there is typically present therein a dentally acceptable substantially water-insoluble polishing agent of the type commonly employed in dental creams, chewable tablets and powders. There is a relatively large number of such materials known in the art. Representative materials include, for example, dicalcium phosphate, tricalcium phosphate, insoluble sodium metaphosphate aluminum hydroxide, magnesium carbonate, calcium carbonate, calcium pyrophosphate, calcium sulfate, polymethyl methacrylate, bentonite, silica gel, precipitated silica, sodium aluminosilicate, etc., including suitable mixtures thereof. It is preferred to use the water-insoluble phosphate salts as the polishing agents and, more particularly, insoluble sodium metaphosphate and/or a calcium phosphate such as dicalcium phosphate dihydrate. Silica gel, precipitated silica and sodium aluminosilicate may be particularly desirable when a visually clear (transparent or translucent) dental cream (or gel) is to be provided.

The polishing agent may be the sole carrier material, particularly when the dentifrice is a toothpowder. Typically, other ingredients are present in the carrier and the amounts of polishing agent are up to about 95 percent by weight of the carrier. In the case of a dental cream or chewable tablet, the polishing agent is generally about 20–75% by weight of the carrier and in a toothpowder it is generally about 70–95% by weight of the carrier.

In the preparation of a toothpowder it is usually sufficient to admix mechanically the ingredients of the carrier with flavoring oil and 5′-ribonucleotide.

In dental cream (or gel) formulations, the liquids and solids should necessarily be proportioned to form a creamy mass of desired consistency which is extrudable from a pressurized container or a collapsible, e.g., aluminum or lead tube. In general, the liquids in the dental cream will comprise chiefly water, or humectants such as glycerine, aqueous solutions of sorbitol, propylene glycol, polyethylene glycol 400, etc., including suitable mixtures thereof. It is advantageous usually to use a mixture of both water and a humectant or binder such as glycerine or sorbitol. The total liquid content will generally be about 20–75 percent by weight of the carrier. A visually clear product may be provided, matching the refractive index of the liquids with that of the polishing agent (e.g. silica gel, precipitated silica or sodium aluminosilicate). It is preferred to use also a gelling agent in dental creams such as the natural and synthetic gums and gumlike materials, e.g., Irish moss, gum tragacanth, sodium carboxymethyl cellulose, polyvinylpyrrolidone, starch, and the like, usually in an amount up to about 10 percent, and preferably about 0.2–5 percent of the carrier. The components of the sialagogue and the flavor modifying agent of the invention are blended into such dental-cream formulation.

In chewable dental tablets the solids and liquids are proportioned similarly to the amounts in dental creams and the sialagogue is blended with the solids and liquids. A waxy matrix such as polyethylene glycol having a molecular weight of about 6,000 is also present, generally in amount of about 4–20 percent by weight, in order to facilitate forming a tablet of desired size and shape.

In other oral compositions, such as mouthwashes and the like, the carrier is an aqueous vehicle which may comprise about 20–99% by weight of the preparation. Typically, the vehicle also includes about 5–30% by weight of a non-toxic alcohol, such as ethanol.

Other oral compositions, such as chewing gums, candies, lozenges, etc., are prepared to include their classic vehicles with flavoring oil and the 5′-ribonucleotide flavor modifying agent.

Organic surface-active agents are used in the vehicle of the present invention to assist in achieving thorough and complete dispersion of the instant compositions throughout the oral cavity, and render the instant compositions more cosmetically acceptable. These agents continue to provide foam even after the inital flash foam provided by the 5′-ribonucleotide is reduced. The organic surface-active material may be anionic, nonionic, ampholytic, or cationic in nature, and it is preferred to employ as the surface-active agent a detersive material which imparts to the composition detersive and foaming properties. Since these agents can contribute to the flavor character of the oral composition compatability of the 5′-ribonucleotide salt with them is particularly noteworthy. Suitable such detergents are water-soluble salts of higher fatty acid monoglyceride monosulfates, such as the sodium salt of the nonosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1, 2-dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last-mentioned amides are N-lauroyl sarcosine, and the sodium, potassium and ethanolinine salts of N-Lauroyl, N-myristoyl or N-palmitoyl sarcosinates, which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface-active materials include nonionic agents such as condensates of sorbitan monostearate with approximately 20 moles of ethylene oxide, condensates of ethylene oxide with propylene oxide condensates of propylene glycol ("Pluronics") and cationic surface-active germicides and antibacterial compounds such as di-isobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure

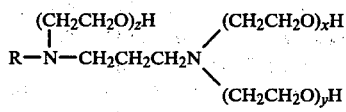

where R is a fatty alkyl group containing from about 12 to 18 carbon atoms, and x, y and z total three of higher, as well as salts thereof with mineral or organic acids.

It is preferred to use the surface-active agent in amount of about 0.5–5% by weight preferably about 0.5–2% of the oral composition.

Various other materials also may be incorporated in the oral composition. Examples thereof are coloring or whitening agents, preservatives, silicones, chlorophyll compounds, ammoniated materials such as urea, diammoniumphosphate and mixtures thereof, and other constituents. These adjuvants are incorporated in the instant compositions in amounts which do not substantially adversely affect properties and characteristics suitably selected, depending upon the particular type of preparation involved.

It may be desirable too to include antibacterial agents in the oral composition, typically in amount of about 0.01–5%, preferably about 0.05–1.0%, by weight of the oral composition. Typical antibacterial agents include:

N¹-(4-chlorobenzyl)-N⁵-(2,4-dichlorobenzyl) biguanide;
p-chlorophenyl biguanide;
4-chlorobenzhydrylguanylurea;
N-3-lauroxypropyl-N⁵-p-chlorobenzylbiguanide;
1,6-di-p-chlorophenylbiguanidohexane;
1-(lauryldimethylammonium)-8(p-chlorobenzyldimethylammonium)octane dichloride;
5,6-dichloro-2-guanidinobenzimidazole;
N¹-p-chlorophenyl-N-laurylbiguanide;
5-amino-1,3-bis(2-ethylhexyl)-5-methylhexahydro pyrimidine; and their non toxic acid addition salts.

The oral compositions of this invention have a pH suitable for use in the oral cavity, typically about 4–10.

The following specific examples are further illustrative of the nature of the present invention, but it is to be understood that the invention is not limited thereto. Amounts and proportions in the examples are by weight unless otherwise indicated.

EXAMPLE 1

The following dental creams were prepared by blending flavor and 5'-ribonucleotides, when present, into the dental cream vehicle:

| INGREDIENTS | PARTS | | |
|---|---|---|---|
| | A | B | C |
| Glycerine | 22.0 | 22.0 | 22.0 |
| Sodium carboxymethyl cellulose | 1.2 | 1.2 | 1.2 |
| Sodium saccharine | 0.2 | 0.2 | 0.2 |
| Sodium benzoate | 0.5 | 0.5 | 0.5 |
| Sodium monofluorophosphate | 0.76 | 0.76 | 0.76 |
| Tetrasodium pyrophosphate | 0.25 | 0.25 | 0.25 |
| Disodium 5'-inosinate (IMP) | — | 0.003 | — |
| Disodium 5'-guanylate (GMP) | — | — | 0.003 |
| Water (deionized) | 24.130 | 24.127 | 24.127 |
| Dicalcium phosphate dihydrate | 48.76 | 48.76 | 48.76 |
| Sodium lauryl sulfate | 1.2 | 1.2 | 1.2 |
| Flavor (Peppermint) | 1.0 | 1.0 | 1.0 |

Experimental tasting beginning two weeks after preparation of the above dental creams and extending over a period of at least two weeks revealed significant perception of mellower flavor in each of the dental creams B and C compared with dental cream A. Flavor notes from the IMP and GMP in dental creams B and C were not detected.

Similar observations would occur when the levels of IMP and GMP in dentifrices are each raised to 0.005 parts (with corresponding reduction in water) and when mixtures of (a) 0.0015 parts of IMP with 0.0015 parts of GMP and (b) 0.0025 parts of IMP and 0.0025 parts of GMP are used. Mellowness can also be detected with each of 0.002 parts of IMP and of GMP and with each of 0.007 parts of IMP and of GMP, although in the latter cases some taste from the IMP or GMP may be detectable.

EXAMPLE 2

The following mouth washes are prepared:

| INGREDIENTS | PARTS | |
|---|---|---|
| | A | B |
| Glycerine | 10.0 | 10.0 |
| Ethyl alcohol | 13.55 | 13.55 |
| Polyoxyethylene (20) sorbitan monoisostearate | 1.0 | 1.0 |
| IMP | 0.003 | — |
| GMP | — | 0.003 |
| Sodium saccharine | 0.04 | 0.04 |
| Flavor (Peppermint) | 1.45 | 1.45 |
| Yellow & red dyes (1% solution) | 0.0046 | 0.0046 |
| Water | Q.S. to 100 | Q.S. to 100 |

Pleasing mellow taste is perceived from these mouthwashes.

EXAMPLE 3

Two dental gels corresponding to each other except that one contains 0.03 parts of a 1:1 mixture of IMP and GMP and the other does not are prepared and agitated to produce foam in accordance with the "sudsing characteristics" test procedure described in U.S. Pat. No. 2,812,284 to Saunders.

The following increases in cubic centimeters of foam volume (ΔF) are observed after the indicated numbers of cycles of shaking for the dental gel containing IMP and GMP.

| Number of Shaking Cycles | ΔF |
|---|---|
| 5 | 15 |
| 10 | 35 |
| 15 | 40 |

| Number of Shaking Cycles | ΔF |
|---|---|
| 20 | 30 |
| 25 | 40 |
| 30 | 0 |
| 60 | 5 |

These results show substantially higher initial (or "flash") foam achieved during early agitation (up to 25 cycles).

Although the invention has been described with reference to specific examples, it will be apparent to one skilled in the art that various modifications may be made thereto which fall within its scope.

We claim:

1. A flavored oral hygiene composition comprising a dental mouthwash, dental cream or dental gel vehicle consisting essentially of a humectant, a flavoring oil in amount to provide flavor characteristic to said composition up to about 5% by weight of said composition and about 0.002–0.007% by weight of a 5'-ribonucleotide.

2. The flavored oral composition claimed in claim 1 wherein said 5'-ribonucleotide comprises an oral composition-compatible salt of 5'-inosinate.

3. The flavored oral composition claimed in claim 1 wherein said 5'-ribonucleotide comprises an oral composition-compatible salt of 5'-guanylate.

4. The flavored oral composition claimed in claim 1 wherein said 5'-ribonucleotide is a mixture of oral composition-compatible salts of 5'-inosinate and 5'-guanylate.

5. The flavored oral composition claimed in claim 4 wherein said mixture is about a 1:1 by weight mixture.

6. The flavored oral composition claimed in claim 1 wherein said flavoring oil is present in amount of about 0.1–1.5% by weight and said 5'-ribonucleotide is present in amount of about 0.003–0.005% by weight.

7. The flavored oral composition claimed in claim 1 wherein about 0.5–5% by weight of organic surface-active agent is present in said oral composition.

8. The flavored oral composition claimed in claim 7 wherein said organic surface agent is present in amounts of about 0.5–2% by weight and is sodium lauryl sulfate.

9. The flavored oral composition claimed in claim 1 wherein said dental vehicle comprises a liquid selected from the group consisting of water, humectant and mixture thereof and a gelling agent, and said oral composition contains about 20–75% by weight of a dentally acceptable substantially water-insoluble polishing agent, said oral composition being a dental cream.

10. The flavored oral composition claimed in claim 1 wherein said dental vehicle is present in amount of about 20–99% by weight of the dentifrice in an aqueous vehicle including about 5–30% by weight, based on the oral composition, of a non-toxic alcohol, said oral composition being a mouthwash.

11. The flavored oral composition claimed in claim 9 wherein about 0.5–2% by weight of sodium lauryl sulfate is present in said dental cream.

12. The flavored oral composition claimed in claim 1 wherein said flavoring oil is peppermint.

* * * * *